US009700588B2

(12) United States Patent
Rommelaere et al.

(10) Patent No.: US 9,700,588 B2
(45) Date of Patent: Jul. 11, 2017

(54) USE OF PARVOVIRUS FOR ELIMINATING CANCER STEM CELLS (CSCS)

(75) Inventors: Jean Rommelaere, Heidelberg (DE); Jeannine Lacroix, Heidelberg (DE); Joerg Schlehofer, Leimen (DE); Olaf Witt, Schriesheim (DE); Elisabeth Hedwig Deubzer, Heidelberg (DE); Sonja Kern, Wuerzburg (DE); Christel Herold-Mende, Bammental (DE); Karsten Geletneky, Heidelberg (DE); Barbara Leuchs, Heidelberg (DE)

(73) Assignees: DEUTSCHES KREBSFORSCHUNGSZENTRUM, Heidelberg (DE); RUPRECHT-KARLS-UNIVERSITAET HEIDELBERG, Heidelberg (DE)

( * ) Notice: Subject to any disclaimer, the term of this patent is extended or adjusted under 35 U.S.C. 154(b) by 188 days.

(21) Appl. No.: 13/807,736

(22) PCT Filed: Jun. 29, 2011

(86) PCT No.: PCT/EP2011/003197
§ 371 (c)(1),
(2), (4) Date: Apr. 11, 2013

(87) PCT Pub. No.: WO2012/003932
PCT Pub. Date: Jan. 12, 2012

(65) Prior Publication Data
US 2013/0209413 A1 Aug. 15, 2013

(30) Foreign Application Priority Data
Jul. 7, 2010 (EP) .................................. 10007007

(51) Int. Cl.
*A61K 39/23* (2006.01)
*A61K 35/768* (2015.01)

(52) U.S. Cl.
CPC .. *A61K 35/768* (2013.01); *C12N 2750/14332* (2013.01)

(58) Field of Classification Search
None
See application file for complete search history.

(56) References Cited

U.S. PATENT DOCUMENTS

| 6,919,196 B1 | 7/2005 | Nueesch et al. |
| 7,179,456 B2 | 2/2007 | Rommelaere et al. |
| 8,450,289 B2 | 5/2013 | Daeffler et al. |

(Continued)

FOREIGN PATENT DOCUMENTS

WO  2009083232 A1  7/2009

OTHER PUBLICATIONS

Blechasz et al., "Parvovirus vectors: use and optimization in cancer gene therapy," Expert Review in Molecular Medicine, vol. 6, Issue 16; pp. 1-24 (2004).*

(Continued)

*Primary Examiner* — Janet L Andres
*Assistant Examiner* — M. Franco Salvoza
(74) *Attorney, Agent, or Firm* — Hultquist, PLLC; Mary B. Grant (57) ABSTRACT

Described is the use of a parvovirus, preferably H-1PV, for the therapeutical elimination of cancer stem cells (CSCs), preferably neuroblastoma stem cells and glioblastoma stem cells.

7 Claims, 6 Drawing Sheets

(56) References Cited

U.S. PATENT DOCUMENTS

| | | |
|---|---|---|
| 2004/0208886 A1 | 10/2004 | Daeffler et al. |
| 2004/0220124 A1 | 11/2004 | Rommelaere et al. |
| 2010/0331815 A1* | 12/2010 | Alt .................... A61K 38/21 604/507 |
| 2012/0009268 A1* | 1/2012 | Asokan et al. ............. 424/499 |

OTHER PUBLICATIONS

Cripe et al., "Targeting Cancer-initiating Cells With Oncolytic Viruses," Molecular Therapy, vol. 17, No. 10: 1677-1682 (2009).*

Lobo et al., "The Biology of Cancer Stem Cells," Annu. Rev. Cell Dev. Biol. 23: 675-99 (2007).*

Ribacka et al., "Cancer, stem cells, and oncolytic viruses," Annals of Medicine, 40: 496-505 (2008).*

Singh et al., "Identification of human brain tumour initiating cells," Nature, vol. 432, 18: 396-400 (2004).*

Robert et al., "Glioblastoma multiforme: a rare manifestation of extensive liver and bone metastates," Biomed Imaging Interv J, 4(1): e3 (2008).*

Wallace et al., "Lymph Node Metastases from Glioblastoma Multiforme," AJNR: 17 (1996).*

Piccirilli et al., "Extra central nervous system metastases from cerebal glioblastoma multiforme in elderly patients. Clinico-pathological remarks on our series of seven cases and critical review of the literature," Tumori, 94: 40-51 (2008).*

Friedman et al., "Temozolomide and Treatment of Malignant Glioma," Clinical Cancer Research vol. 6: 2585-2597 (2000).*

Altaner et al., "Glioblastoma and stem cells," (abstract only) Neoplasma 55(5): 369-74 (2008).*

Stupp et al., "Targeting brain-tumor stem cells," Nature Biotechnology, vol. 25, No. 2: 193-194 (2007).*

Stoica et al., "Identification of Cancer Stem Cells in Dog Glioblastoma," Vet Pathol 46:391-406 (2009).*

Yuan et al., "Isolation of cancer stem cells from adult glioblastoma multiforme," Oncogene 23:9392-9400 (2004).*

Di Piazza, M., et al., "Cytosolic activation of Cathepsins mediates Parvovirus H-1-Induced Killing of Cisplatin and TRAIL-Resistant Glioma Cells", "Journal of Virology", Apr. 2007, pp. 4186-4198, vol. 81, No. 8.

Unpublished U.S. Appl. No. 10/111,970, filed Apr. 29, 2002.

Abschuetz, A., et al., "Oncolytic murine autonomous parvovirus, a candidate vector for glioma gene therapy, is innocuous to normal and immunocompetent mouse glial cells", "Cell Tissue Res.", May 3, 2006, pp. 423-436, vol. 325.

Angelova, A., et al., "Improvement of gemcitabine-based therapy of pancreatic carcinoma by means of oncolytic parvovirus H-1PV", "Clin. Cancer Res.", Jan. 15, 2009, pp. 511-519, vol. 15, No. 2.

Auffinger, B., et al., "Oncolytic virotherapy for malignant glioma: translating laboratory insights into clinical practice", "Front. Oncol.", Feb. 25, 2013, pp. 1-13, vol. 3, Article 32.

Brandenburger, A., et al., "NS-1 and NS-2 proteins may act synergistically in the cytopathogenicity of parvovirus MVMp", "Virology", Feb. 1990, pp. 576-584, vol. 174.

Caillet-Fauquet, P., et al., "Programmed killing of human cells by means of an inducible clone of parvoviral genes encoding non-structural proteins", "EMBO J.", Sep. 1990, pp. 2989-2995, vol. 9, No. 9.

Campos, B., et al., "Differentiation therapy exerts antitumor effects on stem-like glioma cells", "Clin. Cancer Res.", May 4, 2010, pp. 2715-2728, vol. 16, No. 10.

Chen, Y., et al., "Sensitization of human keratinocytes to killing by parvovirus H-1 takes place during their malignant transformation but does not require them to be tumorigenic", "Carcinogenesis", Jan. 1989, pp. 163-167, vol. 10, No. 1.

Friedman, G., et al., "Pediatric glioma stem cells: biologic strategies for oncolytic HSV virotherapy", "Front. Oncol.", Feb. 28, 2013, pp. 1-15, vol. 3, Article 28.

Geletneky, K., et al., "Oncolytic potential of rodent parvoviruses for cancer therapy in humans: a brief review", "J. Vet. Med. B Infect. Dis. Vet. Public Health", Sep.-Oct. 2005, pp. 327-330, vol. 57.

Grimes, C., et al., "Are Cancer Stem Cells Responsible for Cancer Recurrence?", "Cell Biol: Res. Ther.", Jun. 15, 2012, pp. 1-2, doi:10.4172/2324-9293.1000e102.

Lacroix, J., et al., "Parvovirus H1 selectively induces cytotoxic effects on human neuroblastoma cells", "Int. J. Cancer", Sep. 1, 2010, pp. 1230-1239, vol. 127.

Raykov, Z., et al., "Combined oncolytic and vaccination activities of parvovirus H-1 in a metastatic tumor model", "Oncol. Rep.", Jun. 2007, pp. 1493-1499, vol. 17.

Wan, F., et al., "The utility and limitations of neurosphere assay, CD133 immunophenotyping and side population assay in glioma stem cell research", "Brain Pathol.", Feb. 5, 2010, pp. 877-889, vol. 20.

Galli, R., et al., "Isolation and Characterization of Tumorigenic, Stem-like Neural Precursors from Human Glioblastoma", "Cancer Research", Oct. 1, 2004, pp. 7011-7021, vol. 64.

Hiromitsu, H., et al., "The development of therapies targeting cancer stem cells", "Surgery Frontier", 2009, pp. 21-26 (English Excerts From Summary and Other Relevant Descriptions), vol. 16, No. 1.

Singh, S., et al., "Identification of a cancer stem cell in human brain tumors", "Cancer Research", Sep. 15, 2003, pp. 5821-5828, vol. 63.

\* cited by examiner

NB 124 day 9 p. i.    NB 124 day 15 p. i.    IMR-32 day 3 p. i.

NS1→ mock   MOI 1   MOI 50   mock   MOI 1   MOI 50   mock   MOI 1

B

NCH 441          NCH 421          NCH 620          U87 day 9 p. i.   day 15 p. i.   day 9 p. i.   day 15 p. i.   day 9 p. i.   day 15 p. i.   day 3

NS1

NS2 actin→ mock   MOI 50   mock   MOI 50   mock   MOI 50   mock   MOI 50   mock   MOI 50   mock   MOI 50   MOI 10

USE OF PARVOVIRUS FOR ELIMINATING CANCER STEM CELLS (CSCS)

CROSS-REFERENCE TO RELATED APPLICATIONS

This application is a U.S. national phase under the provisions of 35 U.S.C. §371 of International Patent Application No. PCT/EP11/03197 filed Jun. 29, 2011, which in turn claims priority of European Patent Application No. 10007007.7 filed Jul. 7, 2010. The disclosures of such international patent application and European priority patent application are hereby incorporated herein by reference in their respective entireties, for all purposes.

The present invention relates to the use of a parvovirus, preferably H-1PV for the therapeutical elimination of cancer stem cells (CSCs), preferably neuroblastoma or glioblastoma stem cells.

In children, tumors originating from the nervous system are the most frequent solid tumors. Among them, neuroblastoma is the most frequent extra cranial solid tumor. It is derived from progenitor cells of the sympathetic nervous system resulting in highly malignant tumors along the sympathetic chain. High risk neuroblastoma is frequently characterized by a MYCN oncogene amplification and consecutive overexpression of the N-myc Protein. Despite the introduction of multimodal treatment concepts including surgery, radiopharmaceutical treatment by metaiodobenzylguanidine, high-dose chemotherapy with autologous stem cell rescue, local irradiation and retinoic acid maintenance therapy high risk neuroblastoma patients have an extremely poor outcome with long term survival rates of about 30%. These tumors remain a therapeutic challenge and surviving children suffer from treatment related acute and long term toxicities.

Malignant human glioblastomas account for the largest number of human malignant brain tumors. The conventional approaches to treatment of gliomas include neurosurgical techniques (resection or stereotactic procedures), radiation therapy and chemotherapy. Radiation therapy (RT) of malignant gliomas increases the survival of patients by several months but, like other standard therapies, it is unable to prevent tumor recurrence. However, despite these therapies glioblastomas are considered as incurable, since treatment with ionizing radiation, chemotherapy and/or surgical resection achieves only a very limited prolongation of life span of patients. Typically, the average life span after diagnosis is on the order of about 12 to 16 months. Therefore, novel treatment modalities, in particular for neuroblastoma and glioblastoma, are urgently required.

Thus, it is the object of the present invention to provide means for efficient therapy of tumors, preferably neuroblastoma or glioblastoma, which overcome the disadvantages of the current therapies.

According to the invention this is achieved by the subject matters defined in the claims. It was surprisingly found that parvoviruses can be successfully used for efficient therapy by killing of cancer stem cells.

Oncolytic viruses are a promising novel class of cancer cell-specific biological agents, infecting and killing transformed cells while sparing normal tissues. In addition to the oncolytic effect observed both in vitro and in vivo, these viruses also provide immunostimulatory signals inducing the elimination of virus-infected tumor cells. Thereby the innate and adaptive immune systems gain access to tumor antigens, which results in cross-priming and vaccination effects. In neuroblastoma models, a variety of genetically engineered oncolytic viruses have been applied including Newcastle disease virus, attenuated poliovirus, and oncolytic herpes simplex virus 1 and 2.

Some autonomous rodent parvoviruses were shown to preferentially kill transformed and tumor-derived rodent and human cell lines in vitro, while no cytocidal action was observed in non-transformed cells. In particular, H-1PV was found to replicate and exert cytopathic effects in a variety of transformed or tumor derived cells, whereas non-transformed cells remain unaffected in vitro and in vivo. The oncolytic effects of H-1PV observed have been attributed to different cellular death programs, including apoptosis, necrosis of the infected cells or lysosomal membrane permeabilization which causes the release of cathepsins from the lysosomal lumen to the cytosol. The individual mechanism by inducing cellular death in different malignancies seems to depend mainly on the individual cellular background.

H-1PV is a small (20-25 nm), non-enveloped parvovirus containing a linear single-stranded DNA genome of about 5 kb. Its replication in the nucleus is strictly dependent on S-phase-associated factors and the completion of the lytic infectious cycle is tightly dependent on cellular factors that are expressed as a consequence of proliferation and differentiation processes. The non-structural protein NS1 plays an essential role in initiating the parvoviral replication and in inducing its cytotoxicity. Parvoviruses are incapable of inducing quiescent cells to enter S phase, and infection remains cryptic until the host cells enter DNA replication on their own. This dependency on the replication of the host cells accounts, in part, for the tissue specificity, oncotropism, and oncolytic activity of autonomous rodent parvoviruses.

Rats are the natural host of H-1PV, but other rodents such as hamster and mastomys could be experimentally infected. Occasionally, the infection and seroconversion of humans has been reported. H1-PV appears to be non-toxic in humans, even when applied systemically. The oncolytic effects of H-1PV have been studied in vitro and in vivo on a variety of human entities such as lymphoma, pancreatic cancer, glioblastoma cell lines, hepatoma, and breast cancer. However, the oncolytic effect of H-1PV on pediatric tumors had not been studied so far.

In the studies resulting in the present invention a preclinical in vitro assessment of the application of oncolytic H-1PV for the treatment of neuroblastoma cells was performed. Infection efficiency, viral replication, and lytic activity of H-1PV were analyzed in eleven neuroblastoma cell lines with different MYCN status. Oncoselectivity of the virus was confirmed by the infection of short term cultures of non-malignant infant cells of different origin. Mixed culture of glia cells, neuronal cells, astrocytes in short term culture revealed no effect of H-1PV on viability or morphology of the cells. In contrast, a lytic infection was induced in all neuroblastoma cell lines examined at MOIs between 0.001 and 1 pfu/cell. H-1PV actively replicated with virus titres increasing up to 10.000-fold within 48 to 96 hours after infection. The lytic effect of H-1PV was observed independent of MYCN oncogene amplification or differentiation status. Moreover, the expression of viral proteins in a MYCN amplified neuroblastoma cell line correlated with down-regulation of N-myc expression. Infection efficiency, rapid virus replication and exhaustive lytic effects on neuroblastoma cells together with the low toxicity of H-1PV for non-transformed cells, render this parvovirus a promising candidate for oncolytic virotherapy of neuroblastoma.

In summary, the experiments resulting in the present invention show that infection of cancer stem cells, e.g., neuroblastoma stem cells, with parvovirus represents a new and highly effective therapy with only very low side effects. This kind of therapy is even effective regarding CSCs that are resistant to chemotherapy and radiotherapy.

Thus, the present invention provides a parvovirus, preferably a rodent parvovirus for use in a method for therapeutically destroying cancer stem cells (CSCs).

The term "cancer stem cells (CSCs)" as used herein refers to cancer cells (found within tumors or hematological cancers) that possess characteristics associated with normal stem cells, specifically the ability to give rise to all cell types found in a particular cancer sample. CSCs are therefore tumorigenic (tumor-forming), at much lower cell numbers than commonly used cell cultures grown in FCS containing medium. CSCs may generate tumors through the stem cell processes of self-renewal and differentiation into multiple cell types. In the more recent literature the initial term "cancer stem cells" has been replaced by the terms "tumor stem-like cells" or "tumor initiating cells". Thus, the terms "tumor stem-like cells" or "tumor initiating cells" are essentially synonymous to the term "cancer stem cells".

This subfraction of malignant cells within a tumor is characterized by the expression of stem cell markers, such as CD133, nestin and SOX2 for tumor initiating cells of neuroectodermal origin such as glioblastoma or neuroblastoma. For several malignant diseases, among them glioblastoma, it has been shown in vitro and in vivo that conventional cytostatic drug treatment increases the number of cells within this fraction. Therefore, these tumor stem cells have been hypothesized to cause relapse and metastasis by giving rise to new tumors. Therefore, the therapy of the present invention targeted at CSCs improves survival and quality of life of cancer patients, especially for children and for patients with metastatic disease.

The term "therapeutically destroying cancer stem cells" means that the CSCs are killed by the oncolytic and cytotoxic activity of the parvovirus so that the proportion of CSCs within a tumor decreases with the treatment.

The term "parvovirus" as used herein comprises wild-type or recombinant derivatives thereof as well as related viruses or vectors based an such viruses or derivatives. Suitable parvoviruses, derivatives etc. which are useful for gene therapy are known to the person skilled in the art.

In a preferred embodiment of the use of the present invention the CSCs are (a) cancer stem cells resistant to chemotherapy or radiotherapy, or (b) potentially relapsing cancer stem cells.

In a further preferred embodiment of the use of the present invention, said cancer stem cells are neuroblastoma stem cells or glioblastoma stem cells, which represent a model for cancer stem cells of neuroectodermal origin.

In a further preferred embodiment, the parvovirus is a rodent parvovirus, preferably H1, or a related rodent parvovirus such as LuIII, Mouse minute virus (MMV), Mouse parvovirus (MPV), Rat minute virus (RMV), Rat parvovirus (RPV) or Rat virus (RV).

For administration these parvoviruses etc. are preferably combined with suitable pharmaceutical carriers. Examples of suitable pharmaceutical carriers are well known in the art and include phosphate buffered saline solutions, water, emulsions, such as oil/water emulsions, various types of wetting agents, sterile solutions etc. Moreover, in a metastatic rat hepatoma model, H-1 PV could be shown to act as a therapeutic vaccine when being delivered in autologous tumor cells serving as carriers (Raykov et al., 2007). Such carriers can be formulated by conventional methods and can be administered to the subject at a suitable dose. Administration of the suitable compositions may be effected by different ways, e.g. by intravenous, intraperetoneal, subcutaneous, intramuscular, topical or intradermal administration. If infectious virus particles are used which have the capacity to penetrate through the blood-brain barrier, treatment could be performed or at least initiated by intravenous injection of, e.g., H-1 virus. However, long term intravenous treatment could become inefficient by the formation of neutralizing antibodies to H1 virus. Therefore, different modes of intracranial or intratumoral virus application might be preferable. Moreover, after placement of a silicon catheter connected to a small subcutaneous reservoir (Rickham reservoir) during tumor removal or by a separate procedure, parvovirus can be injected locally at various times without further surgery. The parvovirus or derived vectors can also be injected into the CSCs with stereotactic surgery or by targeting with neuronavigation. Combinations of the above mentioned methods of application are also possible.

The dosage regimen will be determined by the attending physician and other clinical factors. As is well known in the medical arts, dosages for any one patient depend on many factors, including the patient's size, body surface area, age, sex, the particular virus, cell etc. to be administered, time and route of administration, general health and other drugs or therapies being applied concurrently.

EXAMPLE 1

Materials and Methods (A) Cell Culture
The human neuroblastoma neurosphere culture NB124 was obtained from Dr. Hedwig E. Deubzer (Clinical Cooperation Unti Pediatric Onocology, German Cancer Research Center). The human glioma stem-like cell lines NCH 421, NCH 441, NCH 620, and NCH 644 were obtained from PD Dr. Christel Herold-Mende from the Department of Neurosurgery (Campos et al., 2010). Basis medium (for stem cells): DMEM (Sigma Aldrich, Munich), 1% penicillin-streptomycin, 1% L-glutamine. Stem cell medium: Basis medium, 20% BIT 100 supplement (provitro GmbH, Berlin), 0.02% bFGF (RELIA Tech GmbH, WolfenbUttel), 0.02% EGF (RELIA Tech GmbH). Trypsin-blocking medium: DMEM (Sigma Aldrich, Munich), 10% heat-inactivated foetal bovine serum, 1% penicillin-streptomycin. Stem-like cells were grown as neurosphere cultures as previously published and cultured at 37° C., 5% $CO_2$ in the respective growth medium (Wan et al., 2010).

(B) Virus Production and Infection

Wild-type H-1PV was produced by infecting NBK-324K human embryonic kidney cells, and purified by filtration (maximal diameter of particles 0.2 μm) and iodixanol gradient centrifugation. The contamination of virus stocks with endotoxins was <2.5 EU/ml. Cells were infected with H-1PV as single cell suspensions after typsin treatment in their respective growth medium at 37° C.

(C) Detection of Infectious H-1PV Particles

Virus titres were determined as described previously (Angelova et al., 2009). Briefly, NB-324K cells ($7.6 \times 10^3$ cells/well) were seeded in 96-well plates 24 h prior to the assay. Cells were infected by 10-fold serial dilutions of the supernatant of the previously infected neurosphere cultures and incubated for 72 h at 37° C., 5% $CO_2$.

After alkaline lysis (0.75 M NaOH), DNA was transferred to a nylon membrane, cross-linked, and hybridized with a NS-1 specific probe radiolabeled with $P^{32}$. Blots were exposed to X-ray film for autoradiography. Titration experiments were always performed in duplicates. Virus was applied at multiplicities of infection (MOI, expressed in plaque-forming units per cell; pfu) as indicated in the text.

(D) Viral DNA Extraction and Quantitative Real-Time PCR

The supernatant of the infected neurosphere cell cultures was collected at different time points after infection. The supernatant was subjected to alkaline lysis in 1 M NaOH in TE buffer for 30 min at 56° C. After neutralization with an equimolar concentration of HCl the samples were diluted 1:100 with sterile water and directly analyzed. Quantification of viral DNA was carried out by real-time qPCR with an NS1-specific TaqMan™ probe (Applied Biosystems by Life Technolgies, Carlsbad (Calif.), U.S.A), using an ABI Prism® 7700 thermal cycler (Applied Biosystems by Life Technolgies, Carlsbad (Calif.), U.S.A) and analyzed by means of SDS 2.1 software (Applied Biosystems by Life Technolgies, Carlsbad (Calif.), U.S.A) as described elsewhere (Abschuetz et al., 2006). Briefly, a DNA fragment of 141 nt within the NS1 gene of H-1PV was amplified, and detected using probe: 5'-6-FAM-ATGCAGCCAG-ACA-GTTA-Q-MGB 3'. A plasmid that contained the NS1-sequence in serial dilutions in the range of $10^1$-$10^8$ copies/reaction was used to standardize the qPCR. Individual reaction mixtures (20 μl) consisted of 1× TaqMan™ Universal PCR Master Mix (Applied Biosystems), 0.3 μM labelled NS1-TaqMan™ probe, 0.3 μM of each primer and 3 μl template. PCR conditions were 2 minutes at 50° C. (destruction of contaminating template by AmpErase™), then 10 minutes 95° C., followed by 40 cycles of denaturation at 95° C. for 15 seconds and annealing/extension at 60° C. for 60 s.

(E) Microscopy

Phase contrast images were generated using an inverted phase contrast microscope (Olympus; Model CKX41) using Cell B software (Olympus Europa GmbH, Hamburg, Germany). Other phase contrast images were obtained using a Leica DFC350 FX™ camera (Leica Microsystems, Wetzlar, Germany) and the Leica FireCam™ software for Macintosh.

(F) Assessment of Cell Viability and Lysis

Proliferation of neuroblastoma cells was tested with the 3-(4,5-dimethylthiazol-2-yl)-2,5-diphenyltetrazolium bromide (MTT) assay as recommended by the manufacturer (Sigma-Aldrich, St. Louis, Mo., U.S.A.). Cells (2,500 cells per well) were cultured in 96-well plates and infected at MOIs indicated in the Figures. After 15 days, cells were washed in PBS and incubated with 0.5 μg/ml MTT-solution for up to 2 hours. After discarding the supernatant and drying the cells, 100 μl isopropanol per well were added. Extinction values were photometrically determined at 570 nm (Multiscan Plus™, Titertek Instruments Inc., Huntsville, Ala., U.S.A.).

Cell lysis was determined by measuring the release of lactate dehydrogenase into culture medium by use of the Cytotox 96 Cytotoxicity Assay Kit™ (Promega Corporation, Madison Wis., U.S.A.)) according to the manufacturer's instructions.

EXAMPLE 2

Figure 1:
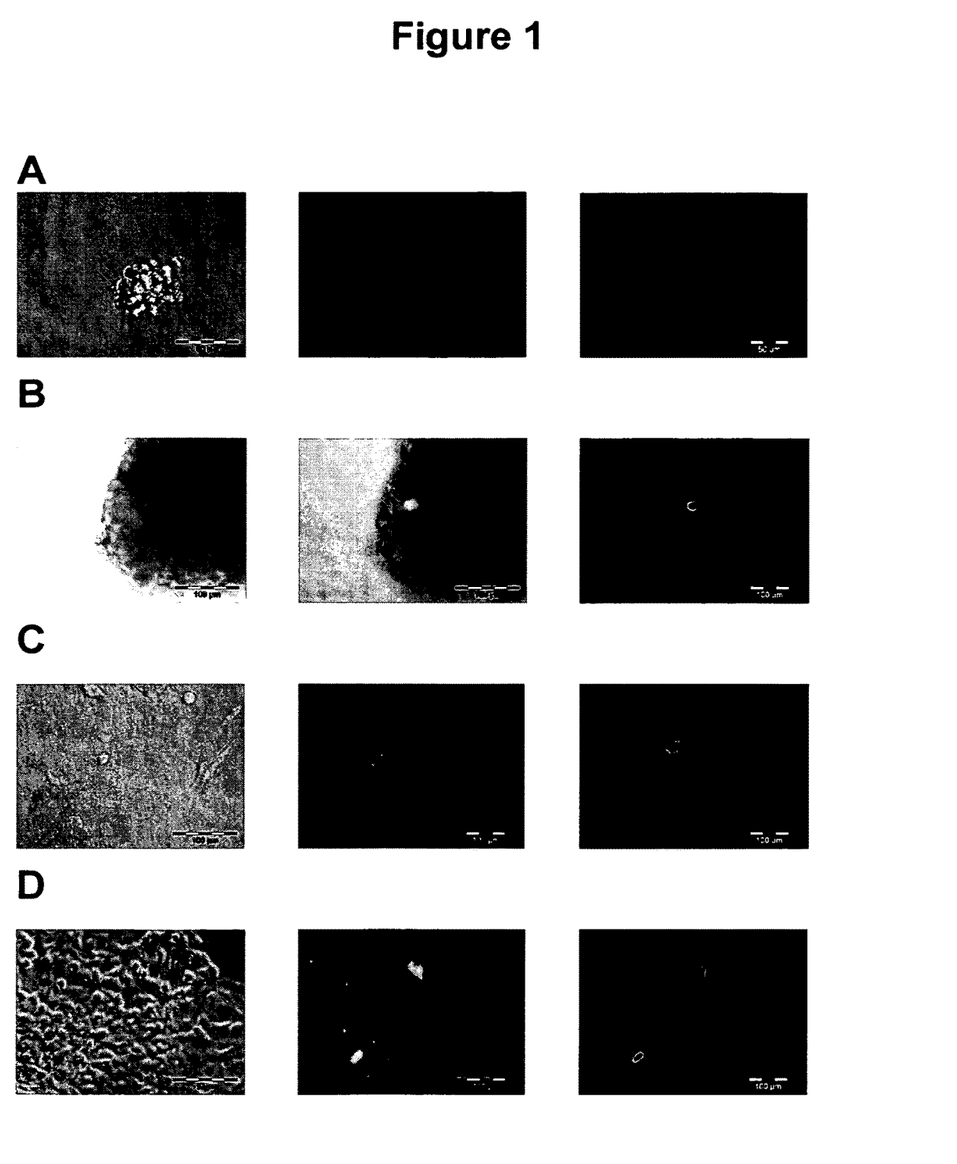
FIG. 1:
(A) NB124, 72 h after infection with MOI 1 H-1EGFP.
(B) NCH 421, 36 h after infection with MOI 50 H-1EGFP.
(C) Kelly, 48 h after infection with MOI 1 H-1EGFP.
(D) IMR-32, 48 h after infection with MOI 1 H-1EGFP.

Neuroblastoma Progenitor and Glioblastoma Stem-Like Cells are Susceptible to H-1PV Infection To determine if H-1PV was able to infect neuroblastoma progenitor cells, NB124 cells were subjected to one replication unit per cell of recombinant, replication-deficient H-1 virus (H-1EGFP) virus expressing GFP. NCH 421 glioblastoma neurospheres were infected with MOI 50 of H-1EGFP. The MYCN amplified neuroblastoma cell lines Kelly and IMR-32 were kindly provided by Prof. Dr. Olaf Witt, CCU Pediatric Oncology, German Cancer Research Center, Heidelberg and served as positive controls. Immunofluorescence microscopy revealed that GFP expression could be detected in both neuroblastoma cell lines and the NB124 neurosphere culture and after infection with H-1EGFP, indicating successful infection of neuroblastoma cells and gene expression driven by the viral promoter in the neuroblastoma progenitor cells infected (FIG. 1, left panel, phase contrast microscopy, middle panel merge, right panel, fluorescence microscopy).

EXAMPLE 3

Figure 2:
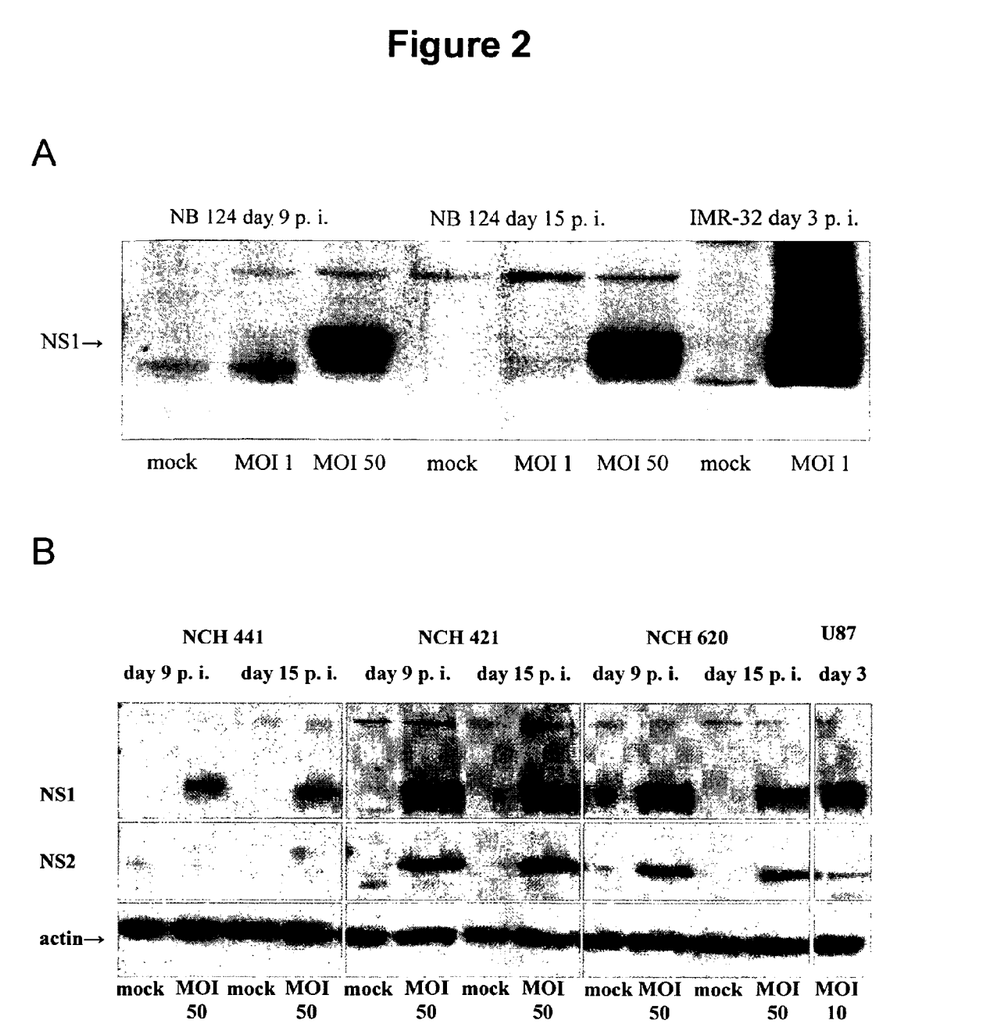
FIG. 2:
(A) NS1 Western Blot of NB 124 neuroblastoma progenitor cells.
(B) NS1 Western Blot of three glioblastoma stem-like cells.

H-1PV Protein Expression Persists in Neuroblastoma Progenitor Cells and High Grade Glioma Stem Cells Up to 15 Days In order to demonstrate that the proteins of wtH-1PV were expressed in infected neuroblastoma and high grade glioma progenitor cells, Western blot analysis of NS1 and NS2 proteins in infected cells was performed. NS1 and NS2 are non-structural proteins required for infection of host cells, and VP1/2 are structural viral capsid proteins (Chen et al., 1989; Caillet-Fauquet et al., 1990, Brandenburger et al., 1990). Following infection with 50 pfu per cell wtH-1PV, these viral proteins were expressed in all stem cell lines investigated, at day 9 and day 15 after infection (FIG. 2A,B). Human neuroblastoma (IMR-32) and glioblastoma (U87) non-stem cell like cell lines served as positive controls. U87 human glioblastoma cells grown under standard conditions served as positive control.

EXAMPLE 4

H-1PV Actively Replicates in Neuroblastoma Progenitor Cells and Glioblastoma Stem-Like Cells In order to address the issue whether H-1PV was able to multiply in neuroblastoma progenitor cells, cells were infected with wtH-1PV. Viral genome copy numbers in the supernatant were determined by real-time PCR in a time period ranging from 3 days up to 21 days after infection. In NB 124 neuroblastoma cells, the viral genome copy numbers increased up to 1,000 fold and the titer of infectious particles even increased up to 100,000 fold indicating highly efficient viral multiplication in these cells. The efficiency of replication of fully infectious viral progeny in these neuroblastoma progenitor cells even exceeded that observed in standard neuroblastoma cell lines which displayed a significant increase in viral copy numbers varying from a $10^2$ to $10^4$ fold increase within 72 to 144 h after infection (Lacroix et al., 2010).

In NCH 421 glioblastoma stem-like cells viral genome copy numbers increased up to 10,000 fold during 21 days after infection, which is comparable to the replication efficiency in other human glioma cell lines without stem-cell properties (Geletneky et al., 2005).

Figure 3:
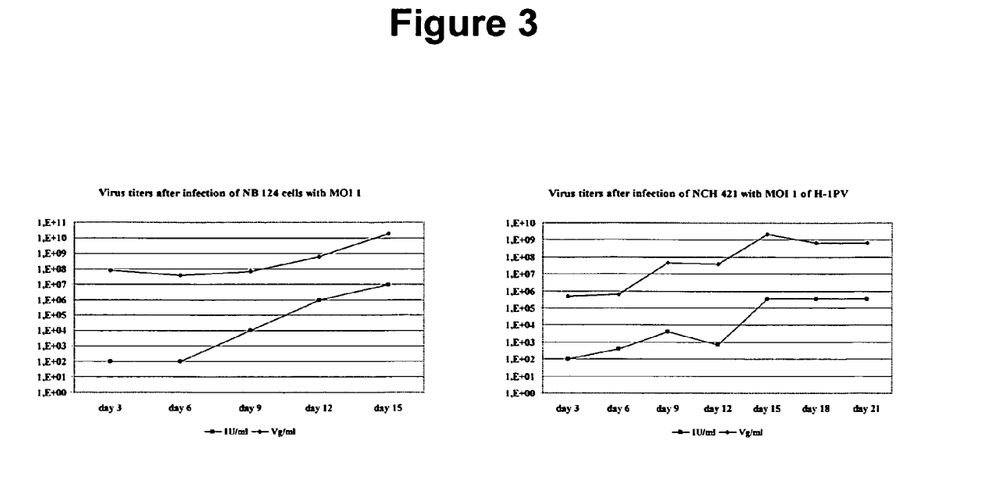
FIG. 3: Infection of neuroblastoma initiating cells and glioblastoma stem-like cells with wtH-1PV
See Example 4 for details.

In order to quantify the generation of infectious progeny H-1PV, infectious particle assays with supernatants of the same infected neuroblastoma progenitor cell line in culture were additionally performed. The progeny H-1 viruses were biologically active, i.e. able to infect NBK-324K cells. In the infection unit assay, a 4,000-fold increase in the neuroblastoma neurosphere culture NB124 and a 3,500-fold increase of infectious particles in the glioma stem-like cell line NCH 421 compared to the input virus could be determined (FIG. 3; upper curve: Vg/ml; lower curve: IU/ml).

Taken together, H-1PV could be proven to productively infect neuroblastoma progenitor cells and glioblastoma stem-like cells. Infection of these cells could be demonstrated to induce the expression of essential viral proteins, efficient viral replication and production of infectious H-1PV progeny.

EXAMPLE 5

Figure 4:
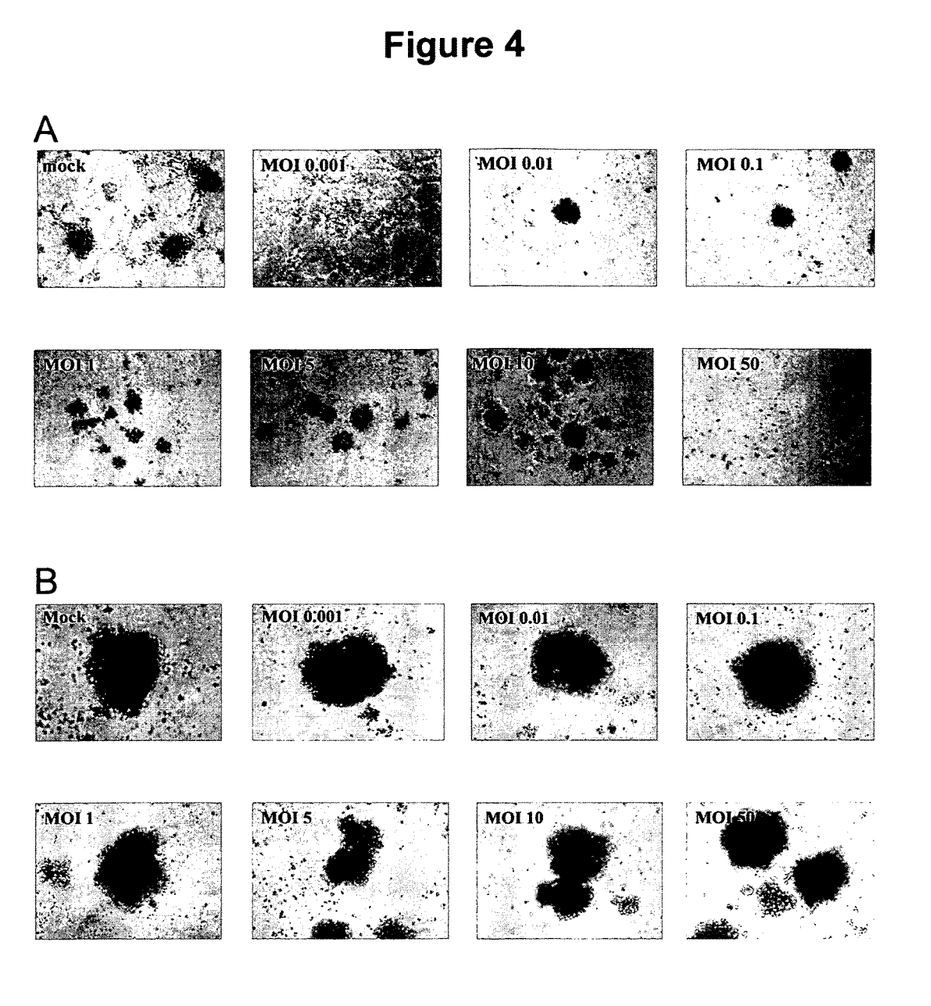
FIG. 4:
(A) Cytomorphology of NB 124, three weeks after infection with wtH-1PV.
(B) Cytomorphology of NCH 421, three weeks after infection with wtH-1PV.

H-1PV Induces Lytic Infection in Neuroblastoma and High Grade Glioma "Stem" Cell Lines In order to test to what extent infection of neuroblastoma cells with wild type H-1PV was lytic, the cytomorphology of the infected cells was documented by phase contrast microscopy. Three weeks after infection H-1PV could be shown to induce significant cytopathic effects on cultured NB124 cells applying an MOI of 0.01 p.f.u. per cell or more (FIG. 4A). Three weeks after infection H-1PV could be shown to induce significant cytopathic effects on cultured NCH 421 cells applying an MOI of 1 p.f.u. per cell or more (FIG. 4B).

EXAMPLE 6

Figure 5:
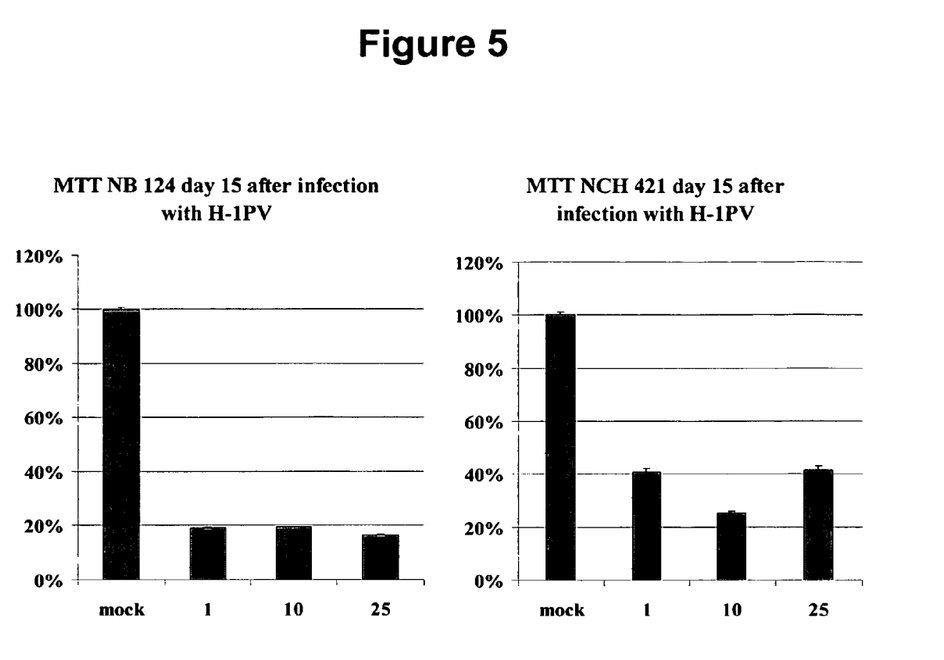
FIG. 5: H-1PV infection significantly reduces cell viability in neuroblastoma initiating and glioblastoma stem-like cells within 15 days after infection
left panel: MTT NB 124 day 15 after infection with H-1PV
right panel: MTT NCH 421 day 15 after infection with H-1PV

H-1PV Infection Significantly Reduces Cell Viability in Neuroblastoma Progenitor and Glioblastoma Stem-Like Cells within 15 Days after Infection H-1PV could be shown to induce significant cytopathic effects on cultured neuroblastoma neurospheres. In order to quantify cytopathic effects with regard to metabolic activity and cellular integrity, MTT test was performed in NB124 and NCH 421 cells 15 days after infection with increasing MOIs of wtH-1PV. Applying an MOI of 1 pfu/cell reduced viable neuroblastoma progenitor cells by 80% and in glioblastoma stem-like cells by 60% within 15 days after infection (FIG. 5).

EXAMPLE 7

Figure 6:
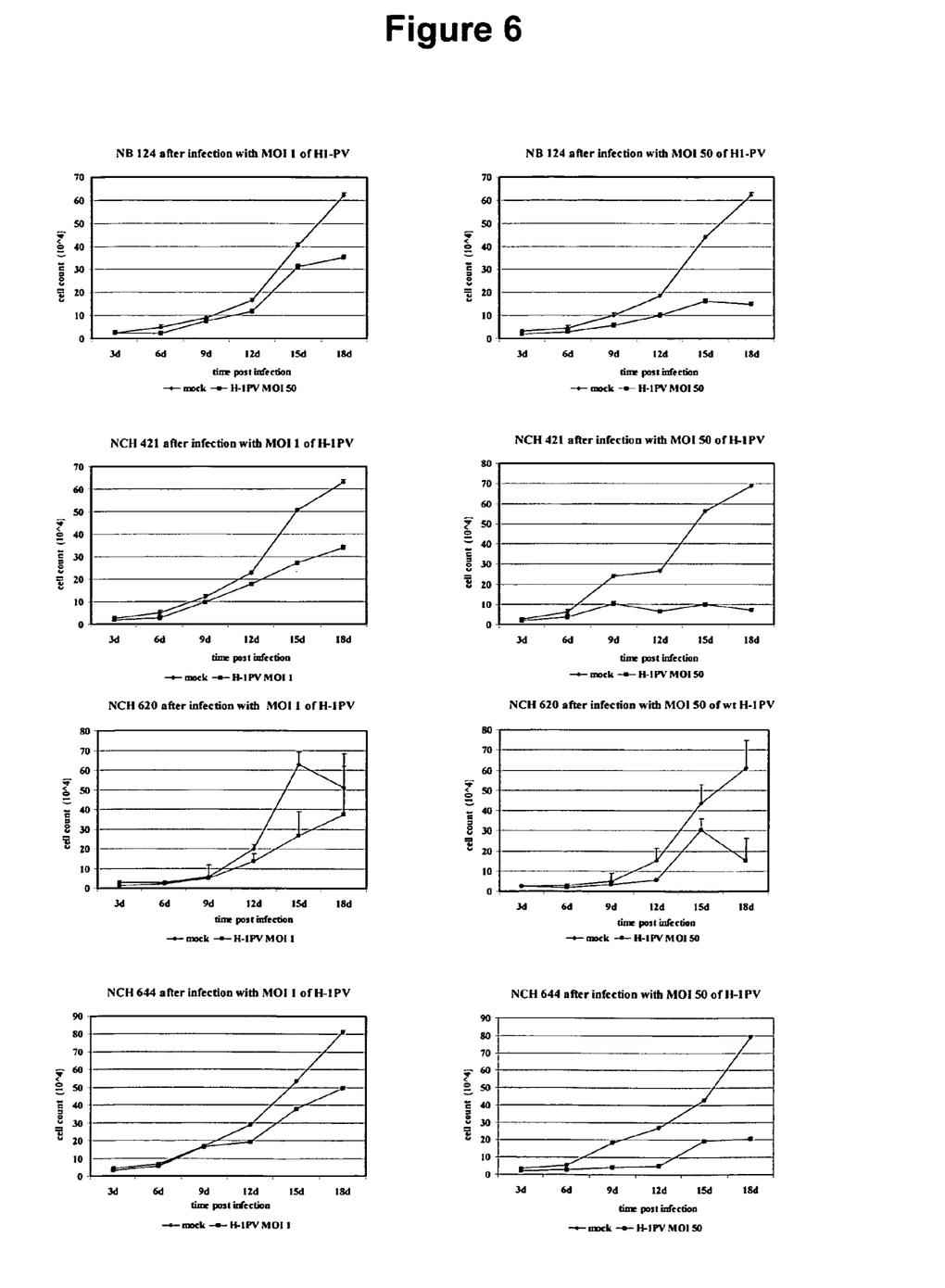
FIG. 6: H-1PV induces cytostatic effects on neuroblastoma initiating cells and on three glioblastoma stem-like cell lines in a dose-dependent manner
See Example 7 for details.
The below examples explain the invention in more detail.

H-1PV Induces Cytostatic Effects on Neuroblastoma Progenitor Cells and on Three Glioblastoma Stem-Like Cell Lines in a Dose-Dependent Manner NB 124 neuroblastoma neurosphere cultures and glioblastoma stem-like cells NCH 421, NCH 620 and NCH 644 were infected with either 1 pfu per cell (FIG. 6, left panel) or 50 pfu per cell (FIG. 6, right panel) and subsequently viable cells were counted in multiplicates of 6 wells per time point. Starting from day 12 to 15 after infection a significant difference in the number of viable cells could be demonstrated for each tumor stem cell line. Applying an MOI of 1 the effect was less pronounced than after application of the higher MOI of 50 p.f.u. per cell (FIG. 6; upper curve: mock; lower curve: H-1PV).

EXAMPLE 8

Cytostatic Effect on "Tumor Stem Cells" does not Seem to be Mediated by Apoptosis Neuroblastoma and high-grade glioma neurosphere cell cultures were analyzed by propidium idodine staining and subsequent flow cytometry for the presence of a sub-G1 DNA content (less that 2n) cell population that is indicative of DNA fragmentation and apoptosis. In parallel Western Blots for the detection of viral proteins such as NS1 were performed. However induction of NS1-expression in NB124 neuroblastoma stem cells nor in high grade glioma "stem" cells neither correlated with G2-arrest nor with the appearance of a sub-G1 population.

REFERENCES

Abschuetz, A., et al. "Oncolytic murine autonomous parvovirus, a candidate vector for glioma gene therapy, is innocuous to normal and immunocompetent mouse glial cells." *Cell Tissue Res.* 325.3 (2006): 423-36.

Angelova, A. L., et al. "Improvement of gemcitabine-based therapy of pancreatic carcinoma by means of oncolytic parvovirus H-1PV." *Clin. Cancer Res.* 15.2 (2009): 511-19.

Brandenburger, A., et al. "NS-1 and NS-2 proteins may act synergistically in the cytopathogenicity of parvovirus MVMp." *Virology* 174.2 (1990): 576-84.

Caillet-Fauquet, P., et al. "Programmed killing of human cells by means of an inducible clone of parvoviral genes encoding non-structural proteins." *EMBO Journal* 9.9 (1990): 2989-95.

Campos, B., et al. "Differentiation therapy exerts antitumor effects on stem-like glioma cells." *Clin. Cancer Res.* 16.10 (2010):2715-27.

Chen, Y. C., et al. "Sensitization of human keratinocytes to killing by parvovirus H-1 takes place during their malignant transformation but does not require them to be tumorigenic." *Carcinogenesis.* 10.1 (1989):163-7.

Geletneky, K., et al. "Oncolytic potential of rodent parvoviruses for cancer therapy in humans: a brief review." *J. Vet. Med. B Infect. Dis. Vet. Public Health* 52.7-8 (2005): 327-30.

Lacroix, J., et al. "Parvovirus H1 selectively induces cytotoxic effects on human neuroblastoma cells." *Int. J. Cancer* (2010).

Raykov, Z., et al. "Combined oncolytic and vaccination activities of parvovirus H-1 in a metastatic tumor model." Oncology Reports 17 (2007): 1493-99.

Wan, F., et al. "The Utility and Limitations of Neurosphere Assay, CD133 Immunophenotyping and Side Population Assay in Glioma Stem Cell Research." *Brain Pathol.* (2010).

The invention claimed is:

1. A method of combating potentially relapsing glioblastoma stem cells in a subject having metastatic glioblastoma, comprising administering to said subject a composition comprising parvovirus H-1 (H-1PV) effective for therapeutically destroying said potentially relapsing glioblastoma stem cells.

2. The method of claim 1, wherein said composition is administered by intravenous (i.v.), intratumoral, intracranial or intracerebral administration.

3. The method of claim 1, wherein said composition further comprises a pharmaceutically acceptable carrier.

4. A method of combating glioblastoma stem cells in a subject suffering from a glioblastoma relapse, comprising administering to said subject a composition comprising parvovirus H-1 (H-1PV) effective for therapeutically destroying said glioblastoma stem cells.

5. The method of claim 4, wherein said composition is administered by intravenous (i.v.), intratumoral, intracranial or intracerebral administration.

6. The method of claim 4, wherein the glioblastoma stem cells are potentially relapsing glioblastoma stem cells.

7. The method of claim 4, wherein said composition further comprises a pharmaceutically acceptable carrier.

* * * * *